United States Patent
Colpas et al.

(10) Patent No.: US 7,566,564 B2
(45) Date of Patent: Jul. 28, 2009

(54) SIGNAL AMPLIFICATION USING A SYNTHETIC ZYMOGEN

(75) Inventors: Gerard J. Colpas, Holden, MA (US); Shite Sebastian, Somerville, MA (US); Mitchell C. Sanders, West Boylston, MA (US)

(73) Assignee: Ethicon, Inc., Somerville, NJ (US)

( * ) Notice: Subject to any disclaimer, the term of this patent is extended or adjusted under 35 U.S.C. 154(b) by 397 days.

(21) Appl. No.: 11/595,275

(22) Filed: Nov. 9, 2006

(65) Prior Publication Data

US 2007/0122873 A1    May 31, 2007

Related U.S. Application Data

(62) Division of application No. 10/570,075, filed as application No. PCT/US2004/028675 on Sep. 2, 2004.

(60) Provisional application No. 60/499,846, filed on Sep. 2, 2003.

(51) Int. Cl.
*C12M 1/34*    (2006.01)
(52) U.S. Cl. .................................... 435/287.1
(58) Field of Classification Search ........................ None
See application file for complete search history.

(56) References Cited

U.S. PATENT DOCUMENTS

| | | |
|---|---|---|
| 5,714,389 A | 2/1998 | Charlton et al. |
| 5,811,252 A | 9/1998 | Verheijen et al. |
| 2003/0096315 A1 | 5/2003 | Sanders |
| 2006/0257955 A1 | 11/2006 | Colpas et al. |

FOREIGN PATENT DOCUMENTS

| | | |
|---|---|---|
| WO | WO 02/16634 A1 | 2/2002 |
| WO | WO 02/082078 A2 | 10/2002 |
| WO | WO 03/063693 A2 | 8/2003 |
| WO | WO 2004/047614 A2 | 6/2004 |
| WO | WO 2004/087942 A2 | 10/2004 |
| WO | WO 2005/042771 A2 | 5/2005 |

OTHER PUBLICATIONS

Jobin et al. "Identification and characterization of four proteases produced by *Streptococcus suis*", FEMS Microbiology Letters, 2003, 220:113-119.*
Enguita, F.J. et al., "Crystal Structure of a Bacterial Endospore Coat Component," *J. Biol. Chem.*, 278(21):19416-19425 (2003).
Plainkum, P., et al., "Creation of a Zymogen," *Nature Struct. Biol.*, 10(2):115-119 (2003).
Saghatelian, A., et al., "DNA Detection and Signal Amplification Via an Engineered Allosteric Enzyme," *JACS*, 125:344-345 (2003).
Verheijen, J.H., et al., "Modified Proenzymes as Artificial Substrates for Proteolytic Enzymes: Colorimetric Assay of Bacterial Collagenase and Matrix Metalloproteinase Activity using Modified Pro-Urokinase," *Biochem. J.*, 323:603-609 (1997).

* cited by examiner

*Primary Examiner*—Jon P Weber
*Assistant Examiner*—Bin Shen
(74) *Attorney, Agent, or Firm*—Roberts Mlotkowski Safran & Cole, P.C.

(57) ABSTRACT

Described herein are zymogens, methods of use for zymogens, and devices that incorporate zymogens. The zymogens include a substrate and an enzyme. The substrate can inhibit the enzyme and is a target for a protein produced by a microorganism. When the substrate is modified by a protein produced by a microorganism, the enzyme is activated. The zymogens can be used to amplify detection assays.

1 Claim, 16 Drawing Sheets
(2 of 16 Drawing Sheet(s) Filed in Color)

| | |
|---|---|
| SSM1 Mutants SEQ ID NO: 9 | MASXXXEGAMFLEAIPMSIPKTLEKFVDAL |
| SSM2 Mutants SEQ ID NO: 10 | MASXXXSASEGAMFLEAIPMSIPKTLEKFVDAL |
| SSM3 Mutants SEQ ID NO: 11 | MASXXXEGAMFLEAIPMSIPKSASTLEKFVDAL |
| SSM4 Mutants SEQ ID NO: 12 | MASEGAMFLEAIPMSIPKTLEKFVDAL |
| T3 Mutants SEQ ID NO: 13 | MASXXXSASVSRRRRRGGSASTLEKFVDAL |

FIG. 8

Lane 1: Kaleidoscope ladder
Lane 2: Clone #SSM1-1 uninduced
Lane 3: Clone #SSM1-1 induced
Lane 4: Clone #SSM1-2 uninduced
Lane 5: Clone #SSM1-2 induced
Lane 6: Clone #SSM1-3 uninduced
Lane 7: Clone #SSM1-3 induced

LIBRARY BASED ON $10^{20}$- possible combinations

SIGNAL AMPLIFICATION USING A SYNTHETIC ZYMOGEN

RELATED APPLICATIONS

This application is a divisional of U.S. application Ser. No. 10/570,075, filed Oct. 11, 2006 which is a U.S. National Stage of International Application No. PCT/US2004/028675, filed 2 Sep. 2004, published in English, and claims the benefit under 35 U.S.C. §119 or 365 to U.S. of America Application No. 60/499,846, filed Sep. 2, 2003. The entire teachings of the above applications are incorporated herein by reference.

BACKGROUND OF THE INVENTION

By amplifying chemical signals, a process that undergoes a chemical reaction can be detected, even at very low concentrations. Such an amplification process has the potential to provide great utility in any field that requires sensitive and/or fast detection of chemical reactions. For example, such a process could be used to detect microorganisms that cause infection and sickness, chemical or bio-warfare agents, or environmental pollutants.

Currently, there are no processes that provide for sensitive and fast detection of chemical reactions. Current methods are either too slow or not sufficiently sensitive. For example, some detection methods can detect the presence of harmful bacteria over the course of a few hours. However, it is often critical to detect pathogens within a few minutes in order to determine that a patient will have infection. The ability to detect the presence of harmful bacteria before the onset of infection would allow the healing of wounds and burns to occur both faster and with fewer complications. Furthermore, after patients are discharged from the hospital, they become responsible for monitoring their own healthcare, and the symptoms of infection may not be evident to the unskilled patient. Rapid identification of dangerous bacterial strains would allow the prescription of the most appropriate treatment and prevent the overuse of broad-spectrum antibiotics resulting in improved patient outcomes and a reduction in the development of antibiotic resistant strains of bacteria.

Severe burns are a major reason for admission to intensive care units. Currently, patients with total burns over 20% of body surface have a mortality rate of 22%. Although modern antimicrobial therapy has improved the outcome for serious burn patients, infections continue to be a major cause of morbidity and mortality in patients surviving the shock phase of a thermal injury. Despite antibiotic therapy and improved asepsis, often the control of infection is not completely successful. Infection is also one of the main causes of the patient's suffering, poor healing of wounds, extensive tissue destruction, and serious local and systemic complications. Therefore, control of infection in a severely burned patient plays an important role in prognosis, because the onset of serious infection may lead to the patient's death, either directly or through related mechanisms (e.g., the postponement of surgery because of poor general conditions).

Nosocomial infections are of serious concern for hospitals, as many patients are weak or immuno-compromised and susceptible to significant morbidity and mortality. Colonization rates are significantly higher in the hospital setting, both among healthcare workers, and among patients. Moreover, the colonizing organisms in the hospital environment are likely to be resistant to many forms of antimicrobial therapy, due to the strong selective pressure that exists in the nosocomial environment, where antibiotics are frequently used. It is estimated that there are more than 2 million hospital-acquired infections each year that could have been prevented by proper hand washing and rapid detection systems for microbial pathogens. These infections can be deadly to many patients. For example, elderly patients who develop a blood-borne infection due to catheterization have more than a 50% mortality rate. Unfortunately, many symptoms are only evident after the infection is already established.

The possibility that food or waterborne pathogens will be encountered in third world countries or unleashed in a bio-terrorism attack is problematic given the state of current technology. Many common causes of illness are capable of infecting the very young or elderly through contaminated water or food, even at very low concentrations (as few as 10 to 100 cells of *Shigella, Salmonella*, or *E. coli* O157:H7 can cause illness or death). A method that provides for early detection of such contaminants would be beneficial since current methods require a lengthy sampling and collection time to properly detect the presence and identity of pathogens. Early detection would reduce the number of food recalls and poor brand recognition (for example, when a processing plant is shut down by the USDA).

In this era of resistant bacteria and bio-weapons, the rapid detection and identification of human pathogens and biological toxins is crucial so that the most appropriate medical response can be implemented. Early detection requires some method of signal amplification, as biological agents can infect in such minute quantities that the agents may go unnoticed by other non-amplified techniques. It would be useful to have a signal amplification method that would surpass existing detection and identification systems in their speed and simplicity.

SUMMARY OF THE INVENTION

This invention relates to zymogens, and their use in detection assays and devices.

In some embodiments, this invention features methods for detecting modification of a peptide. In one embodiment, the method comprises the steps of exposing a zymogen to a sample, and detecting the modification or an absence of the modification. The zymogen includes an exogenous peptide and a signal enzyme that is inhibited by the exogenous peptide. The exposure occurs under conditions that will facilitate a modification of the exogenous peptide. The modification includes cleaving the exogenous peptide, and the cleavage results in activation of the signal enzyme and a detectable signal. Some examples of suitable signal enzymes include green fluorescent protein (GFP), luciferase, laccase (CotA), and horseradish peroxidase (HRP).

In another embodiment, the method comprises the steps of exposing a structure to a sample, and detecting the modification or absence of the modification. The structure includes an exogenous peptide and at least one cofactor. The exposure occurs under conditions that will facilitate a modification of the exogenous peptide. The modification includes cleaving the exogenous peptide, and the cleaving results in the cofactor activating a zymogen to produce a signal enzyme. The cleaving also resulting in a detectable signal.

In another embodiment, the method comprises the steps of exposing an exogenous peptide to a sample and detecting the modification or an absence of the modification. The exogenous peptide is attached to at least two enzymes and the exogenous peptide inhibits the enzymes. The exposure occurs under conditions that will facilitate a modification of the exogenous peptide. The modification includes cleaving the exogenous peptide, and the cleavage results in activation of the enzymes and a detectable signal.

In further embodiments, the method comprises the steps of exposing a complex to a sample and detecting the modification or an absence of the modification. The complex includes at least one exogenous peptide and at least two enzymes that are inhibited by the exogenous peptide. The exposure occurs under conditions that will facilitate a modification of the exogenous peptide. The modification includes cleaving the exogenous peptide, and the cleavage results in a detectable signal.

In more embodiments, the method comprises the steps of exposing a zymogen to a liquid sample and detecting the modification or an absence of the modification. The zymogen includes an exogenous peptide and a signal enzyme that is inhibited by the exogenous peptide. The zymogen is attached to a solid surface at an attachment point, and the exposure occurs under conditions that will facilitate a modification of the exogenous peptide. The modification includes cleaving the exogenous peptide and the cleavage results in activation of the signal enzyme, detachment of the signal enzyme from the solid surface, and a detectable signal.

In still more embodiments, this invention features a synthetic zymogen comprising an enzyme covalently bonded to an exogenous peptide in such a way that the exogenous peptide inhibits an enzymatic activity of the enzyme. The exogenous peptide includes a target of an enzyme produced by a microorganism.

As used herein, a "target" is a protein, peptide, or portion of a protein or peptide that acts as a substrate. That is, a target is a peptide, protein, or portion thereof that an enzyme binds and/or acts upon.

In further embodiments, this invention features a zymogen complex comprising at least two enzymes, each covalently bonded to an exogenous peptide, the exogenous peptide inhibiting an enzymatic activity of each enzyme.

In still more embodiments, this invention features testing devices. In one embodiment, the testing device comprises a membrane, at least one peptide attached to the membrane, a signal enzyme attached to the peptide, and at least one detectably labeled substrate attached to the membrane at a second location. The peptide comprises a substrate for an enzyme produced by a microorganism, and the detectably labeled substrate comprises a target for the signal enzyme.

In further embodiments, the testing device comprises a solid surface, a peptide substrate attached to the solid surface, and a zymogen attached to the peptide substrate. The zymogen includes a signal enzyme that is inhibited by the peptide substrate.

In some embodiment, this invention features a synthetic zymogen comprising *Bacillus subtilis* CotA with an exogenous peptide (non-native peptide) inserted into the active site (catalytic site) of the zymogen, wherein the inserted peptide inhibits the enzymatic activity of the zymogen. The inserted peptide can also comprise a target peptide substrate specific for an enzyme produced by a microorganism of interest (to be detected in a sample). The microorganism of interest is a microorganism selected from the group consisting of: bacteria, viruses, fungi and mold.

In further embodiments, this invention features a *Bacillus subtilis* CotA mutant (variant) comprising CotA with an exogenous peptide consisting of the reactive side loop of alpha-1 proteinase inhibitor wherein the peptide inhibits laccase activity.

In still more embodiments, this invention features a sensor for the detection of a microorganism comprising a synthetic zymogen.

In further embodiments, this invention features a method of detecting a signal from a reaction comprising the use of a synthetic zymogen, wherein the reaction comprises the degradation of an exogenous peptide inserted into the zymogen and whereupon degradation of the inserted peptide the enzymatic activity of the zymogen is reactivated resulting in the catalysis of a zymogen-specific substrate and the generation of a detectable signal. The reactivation of the zymogen can result in multiple zymogen-specific substrate catalytic reactions and thus multiplies (amplifies) the signal generated from the degradation of the inserted exogenous peptide. The detectable signal can be, for example, a colorimetric or fluorescent signal.

In some embodiments, this invention features a synthetic zymogen complex comprising one or more synthetic zymogens, wherein the zymogens are coupled (attached or linked) by a peptide comprising a target peptide substrate specific for both a microorganism of interest and for the zymogen. The enzymatic activity of the zymogen can be, for example, laccase, phenol oxidase, or multi-copper oxidase activity. In one embodiment, the synthetic zymogen complex comprises *Bacillus subtilis* CotA.

In some embodiments, this invention features a sensor for the detection of a microorganism comprising a synthetic zymogen complex.

In still more embodiments, this invention features a method of amplifying a signal from a reaction comprising the use of a synthetic zymogen complex, wherein the reaction comprises the degradation of the linking peptide and whereupon degradation of the linking peptide the linked zymogens are released from each other and substantially simultaneously the enzymatic activity of the released zymogens is reactivated resulting in multiple zymogen-specific substrate catalytic reactions and the amplification of a signal.

In further embodiments, this invention features a synthetic zymogen comprising a non-protease enzyme with an exogenous protease peptide (non-native peptide) inserted into the active site (catalytic site) of the zymogen, wherein the inserted peptide inhibits the enzymatic activity of the zymogen.

In another embodiment, this invention features a method of manufacturing a synthetic zymogen comprising inserting an exogenous protease peptide in the active site (catalytic site) of a non-protease zymogen, wherein the inserted peptide inhibits the enzymatic activity of the zymogen.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The patent or application file contains at least one drawing executed in color. Copies of this patent or patent application publication with color drawings will be provided by the Office upon request and payment of the necessary fee.

FIG. 8 illustrates CotA mutagenesis, including SSM1 Mutants (SEQ ID NO: 9), SSM2 Mutants (SEQ ID NO: 10), SSM3 Mutants (SEQ ID NO: 11), SSM4 Mutants (SEQ ID NO: 12), and T3 Mutants (SEQ ID NO: 13).

DETAILED DESCRIPTION OF THE INVENTION

Figure 1:
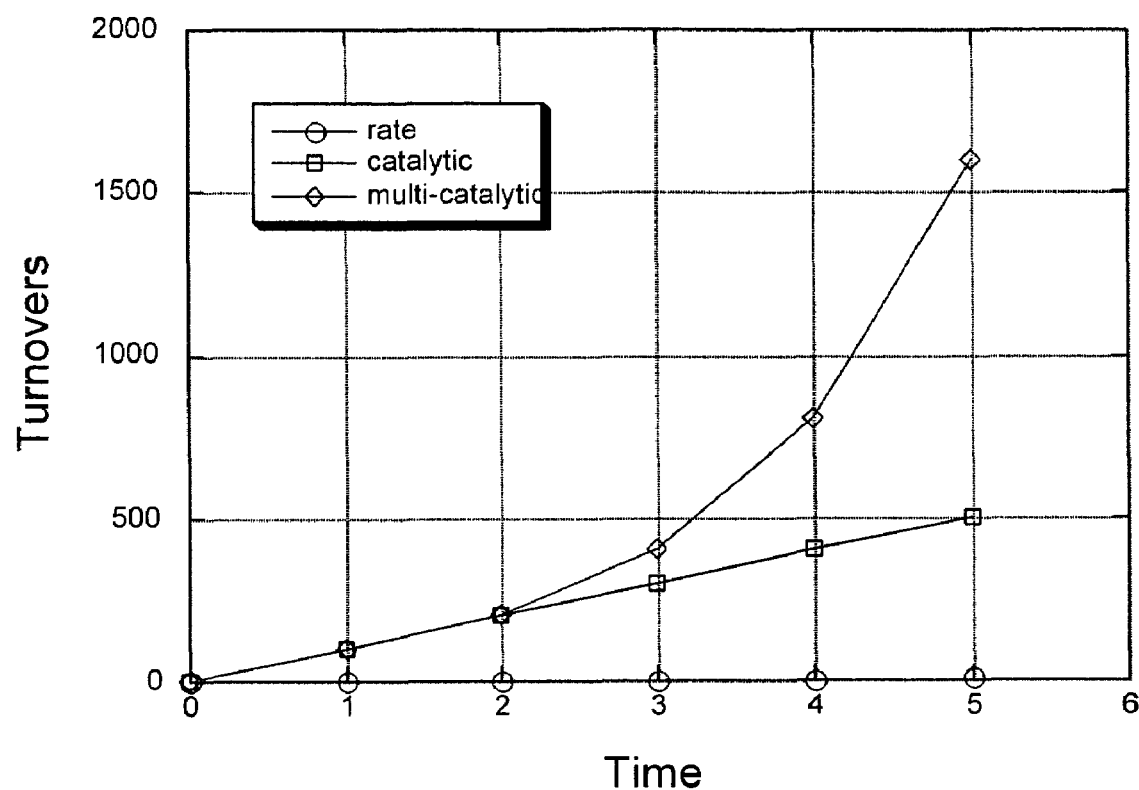
FIG. 1 illustrates a comparative example of the results that can be obtained with some of the amplification mechanisms of this invention.

A description of preferred embodiments of the invention follows. While this invention has been particularly shown and described with references to preferred embodiments thereof, it will be understood by those skilled in the art that various changes in form and details may be made therein without departing from the scope of the invention encompassed by the appended claims.

This invention relates to signal amplification systems for sensors that detect chemical reactions (e.g., bio-pathogen sensors). By utilizing a multi-step catalytic cascade of reactions, this invention provides for fast and accurate detection of chemical reactions or agents. For example, this invention can be used to detect toxins, proteases, or proteins produced by microorganisms (e.g., viruses, bacteria, or fungi). The signal from a microbial protein (e.g., a protease or other enzymes) can be amplified and detect in seconds with a detection assay (e.g., a calorimetric assay). This invention can also be used to detect microbial contamination and/or infection. This invention provides for liquid or solid phase detection systems (e.g., pathogen sensors or sensor systems) that surpass existing detection and identification systems in their speed, accuracy, and/or sensitivity. The sensors and sensor systems can be used for aerosol samples as well. The invention can be useful for both military and medical applications.

Microorganisms (e.g., bacteria) secrete or produce enzymes, and some of these enzymes are specific or unique to the producing or secreting microorganism. As such, some enzymes produced by microorganisms can act as a "fingerprint" or target and can be used as a marker or indicator for detection assays. Some of these targets have been used to produce rapid and specific assays for *Enterococcus faecalis, Escherichia coli, Pseudomonas aeruginosa, Staphylococcus aureus, Streptococcus pyogenes* and several others. Since a very small amount of enzyme can turn over a large amount of substrate under the proper conditions, an enzyme-based sensor can achieve a level of sensitivity not possible with simple antibody-based techniques. Briefly, these sensors and detection assays detect the presence of microorganisms by interacting with a protein (e.g., a protease or other enzyme) secreted or expressed by a microorganism (e.g., a bacteria or fungi). For example, the sensors can include a peptide or substrate that is designed to interact with an enzyme that is specific to a microorganism of interest. When the substrate of the sensor contacts or interacts with the enzyme, the peptide is cleaved or modified in such a way that a detectable signal is produced.

In one example, the substrate is labeled with two different dyes, with one dye serving to quench fluorescence resonance energy transfer (FRET) to the other when the dye molecules are in close proximity. FRET is the process of a distance dependent excited state interaction in which the emission of one fluorescent molecule is coupled to the excitation of another. A typical acceptor and donor pair for resonance energy transfer consists of 4-(4-(dimethylamino)phenyl)azo benzoic acid (DABCYL) and 5-[(2-aminoethylamino)] naphthalene sulfonic acid (EDANS). EDANS is excited by illumination with light at a wavelength of around 336 nm, and emits a photon with wavelength around 490 nm. If a DABCYL moiety is located within 20 angstroms of the EDANS, this photon will be efficiently absorbed. DABCYL and EDANS will be attached to opposite ends of a peptide substrate. If the substrate is intact, FRET will be very efficient. If the peptide has been cleaved by an enzyme, the two dyes will no longer be in close proximity and FRET will be inefficient. The cleavage reaction can be followed by observing either a decrease in DABCYL fluorescence or an increase in EDANS fluorescence (loss of quenching). In this manner, the presence of the specific enzyme, and hence the presence of the enzyme-producing microorganism, is detected.

In another example, the substrate is attached to two colorimetric components. One of the colorimetric components can be a first color, for example, blue, and the second colorimetric component can be a second color, for example, yellow. When present on the same substrate, the unmodified substrate can appear green. If that same substrate is modified (e.g., by enzymatic cleavage of the yellow calorimetric component from the substrate) the substrate can appear blue. Hence, the modification of the substrate would be signaled by a change in color from green to blue.

In another example, a substrate is labeled with one colorimetric component and attached to a solid support that is colored. The calorimetric component can be a first color, such as yellow, and the solid support can be a second color, such as blue. The combination of the solid support with the unmodified substrate can appear green. If the substrate is modified (e.g., by enzymatic cleavage of the yellow colorimetric component from the substrate), the combination of the solid support and the modified substrate will appear blue. Hence the modification of the substrate would be signaled by a change in color from green to blue.

The present invention can be used to amplify or improve the sensors and detection assays described above. However, those of skill in the art will recognize that other sensors and detection assays can also be used in conjunction with the present invention. Some examples of sensors and detection assays to which the present invention can be applied or incorporated are described in U.S. patent application Ser. No. 09/848,781, filed on May 3, 2001, published on May 22, 2003, as U.S. Patent Application Publication No. 2003/0096315 A1, and entitled "Device for Detecting Bacterial Contamination and Method of Use"; International Application No. PCT/US03/03172, filed on Jan. 31, 2003, published on Aug. 7, 2003, as International Publication Number WO 03/063693 A2, and entitled "Method for Detecting Microorganisms"; International Application No. PCT/US2003/037319, filed on Nov. 21, 2003, published on Jun. 10, 2004, and entitled "Methods, Biosensors and Kits for Detecting and Identifying Fungi"; International Application No. PCT/US2004/002594, filed on Jan. 31, 2004, and entitled "Method for Detecting *Escherichia Coli*"; U.S. Provisional Application No. 60/444,523, filed on Jan. 31, 2003, and entitled "Method For Detecting *Escherichia Coli*"; and U.S. Provisional Application No. 60/578,502, filed on Jun. 9, 2004, and entitled "Colorimetric Substrates, Colorimetric Sensors, and Methods of Use." The entire teachings of each of these applications are incorporated herein by reference.

This invention provides for amplification of a signal using catalysis to multiply or increase the potential number of catalytic turnover events (i.e., catalytic reactions). In some embodiments, this invention uses enzyme catalysis to multiply each turnover event of a microbial protein (e.g., a bacterial toxin or protease). In other embodiments, this invention provides for further amplification by using a multi-catalytic or "chain reaction" mechanism to increase the amount of enzyme that can be activated with each turnover event. FIG. 1 illustrates a comparative example of the results that can be obtained with these amplification mechanisms. The trend line labeled "rate" represents the turnovers obtained without the use of a catalyst of the invention. The trend line labeled "catalytic" represents the turnovers obtained using enzyme catalysis to multiply each turnover event. The trend line labeled "multi-catalytic" represents the turnovers obtained the use of a multi-catalytic or "chain reaction" mechanism to increase the amount of enzyme that can be activated with each turnover event.

In some embodiments, the invention is a signal amplification that utilizes enzyme catalysis to multiply each turnover event of a microbial protein (e.g., a microbial toxin, such as a protease or other enzyme produced by a microorganism). For example, a peptide containing a target sequence of a microbial protein of interest is linked or joined to a signal enzyme in such a way that the enzymatic activity of the enzyme is inhibited. In other words, the peptide is bonded or incorporated into the signal enzyme, thereby yielding a zymogen (i.e., an inactive enzyme precursor). The inhibition of the signal enzyme can be accomplished by, for example, attaching a molecule to the signal enzyme that sterically blocks the active site of the signal enzyme or by causing the signal enzyme to fold into an inactive confirmation. In one embodiment, a blocking molecule is attached to the signal enzyme by disulfide bonds.

This inhibited complex can be reactivated, for example, by a microbial protein (e.g., a bacterial protease) that recognizes the peptide sequence as a substrate. The microbial protein cleaves the peptide portion of the zymogen, thereby activating the signal enzyme. The signal enzyme can then begin to turn over a labeled substrate (e.g., a labeled substrate described above) to produce a detectable signal, such as a colorimetric or fluorescent signal. In this manner, each individual peptide cleavage event can be multiplied by the reactivated signal enzyme into a large number of turnovers in a short period of time.

Figure 2:
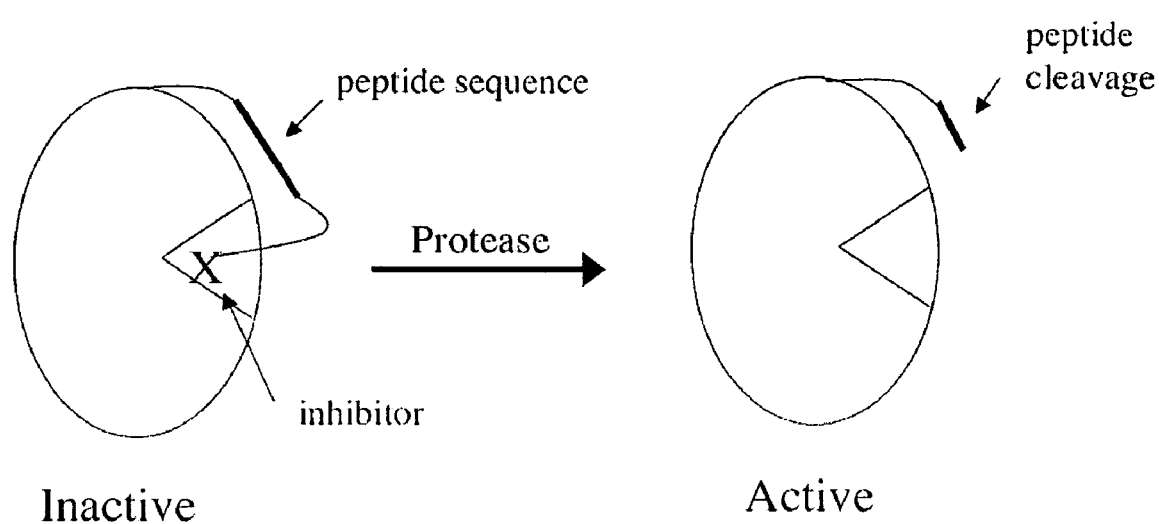
FIG. 2 illustrates one example of a graphical representation of the general mechanism behind one embodiment of a catalytic amplification.

FIG. 2 illustrates one example of a graphical representation of the general mechanism behind this catalytic amplification. On the left, a zymogen includes a peptide sequence and an inhibitor. The inhibitor is sterically blocking an active site, rendering the signal enzyme portion of the zymogen inactive. The zymogen encounters a protease, which cleaves the peptide sequence. The cleaved portion of the peptide, along with the inhibiting portion, moves (e.g., migrates or diffuses) away from the active site, thereby removing the inhibition and activating the signal enzyme. The signal enzyme is then free to catalyze a labeled substrate, thereby producing a detectable signal.

In other embodiments of this invention, alternate or supplemental signal enzyme activation mechanisms are utilized to amplify a signal for a detection assay or sensor. For example, enzymatic activity can be regulated by controlling the availability of a cofactor that is required by the signal enzyme for catalysis. This is a suitable mechanism for many signal enzymes that can produce a calorimetric or fluorescent signal. In some embodiments, metal ion cofactors are locked up in a structure that can be released by a peptide cleavage reaction. Cleaving the peptide releases the metal ions, and activates numerous enzymes. In this way, many signal enzymes can be activated at once, thereby multiplying the resulting signal.

In some embodiments, this invention utilizes a multi-catalytic or "chain reaction" mechanism to increase the number of signal enzymes that can be activated with each turnover event, thereby yielding an amplified signal from a detection assay or sensor. For example, a peptide can couple two or more signal enzymes in such a way so as to sterically hinder the signal enzymes while maintaining the availability of the peptide to interact with a microbial protein (e.g., so that it can be cleaved by a bacterial protease). The coupled signal enzymes can be the same, similar, or different. In some embodiments, the peptide sequence is designed to be a suitable substrate for both the microbial protein and one or more of the coupled enzymes.

Figure 3:
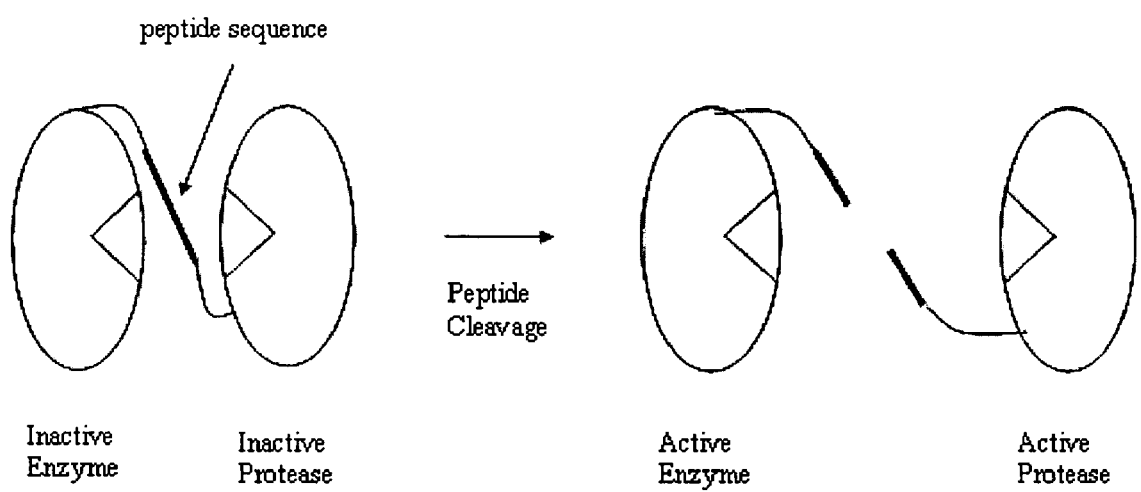
FIG. 3 illustrates one example of a graphical representation of the general mechanism behind one embodiment of a multi-catalytic amplification.

FIG. 3 illustrates one example of a graphical representation of the general mechanism behind this multi-catalytic amplification. On the left, a peptide sequence couples two inactive signal proteins, with one signal protein being an inactive enzyme and the other signal protein being an inactive protease. The peptide coupling the two signal proteins has rendered them inactive. After the zymogen/peptide complex encounters a microbial peptide (e.g., a bacterial protease), the peptide sequence is cleaved (e.g., through hydrolysis), thereby activating both signal proteins. The now active enzyme is then free to catalyze a detectably labeled substrate to produce a signal. The now active protease is free to catalyze the cleavage of peptides that are inhibiting other signal proteins, thereby multiplying turnover events even further. In this way, the detectable signal of the detection assay or sensor is amplified. The result is a signal amplification that would provide a relatively larger increase in the rate of amplification with time compared to detection assays that are based upon a mechanism where a microbial protein interacts solely or directly with a detectably labeled substrate or compared to catalytic amplification that utilizes a single signal enzyme activation step. A similar mechanism can be used, for example, for a hydrolytic enzyme with a fluorescent substrate.

In some embodiments, one or more of the previously described amplification methods are used in conjunction, and/or with, a detection assay that is based on a mechanism where a microbial protein interacts directly with a detectably labeled substrate. For example, in one embodiment, this invention utilizes a multi-catalytic zymogen/peptide complex along with a single zymogen and/or with a signal enzyme activation process that is regulated by controlling the availability of a cofactor that is required by the signal enzyme for catalysis.

Zymogen Design

In designing or choosing a suitable zymogen for use in the various embodiments of the present invention, several factors can be considered, including:

1. The difference in activity between the zymogen and the signal enzyme. Preferably, the difference in activity is large enough to provide the desired signal resolution.

2. The type of assay with which the zymogen will be used. Preferably, the assay is economical and not unnecessarily complex for the application of interest.

3. The sensitivity of the zymogen. Preferably, the zymogen is sufficiently sensitive to the presence of the microbial protein of interest so that the detection assay provides a suitable signal when the number of microorganisms that are to produce a detectable signal are present.

4. The activation mechanism. Preferably, the zymogen is activated by the desired mechanism (e.g., proteolytic activation).

5. The activation site. Preferably, the activation site is configured in a way that allows it to specifically interact with a detectably labeled substrate or other means for producing a detectable signal.

Some or all of these criteria may be important, depending on the specific application or microorganism to be detected. The construction or selection of a zymogen to meet these or other criteria can be done by mutagenesis of a suitable enzyme to attach the peptide and inhibitor (or protease) regions. Once this is constructed, random mutagenesis can be used to refine the inhibition and activation properties of the resulting zymogen.

Figure 4:
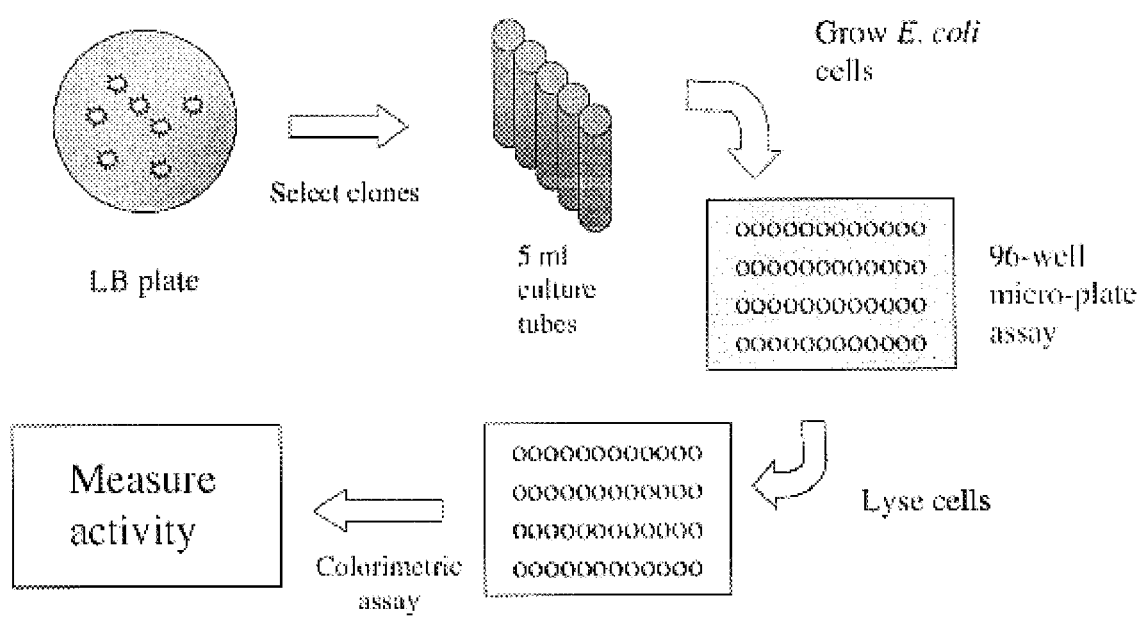
FIG. 4 illustrates a general initial in vitro zymogen screening strategy.

It is advantageous to use a rapid screening method to identify the mutations that would be suitable for use as a zymogen in an amplification process of the invention. For example, the measurement of activity can be done in a sequential manner, first for inhibition and then again after reactivation. FIG. 4 illustrates a general initial in vitro screening strategy, which can include the steps of:

1. The cells are grown overnight in LB medium at 37° C.

2. Following induction with 1 mM IPTG, the cells are lysed and bound to epitope tag binding plates (e.g., nitrilotriacetic acid or antibody coated plates).

3. The plates are then washed 3× with phosphate buffered saline (PBS).

4. The cells are then incubated with bacterial proteases to measure the reactivation of the CotA zymogen mutants.

5. The mutants that produce the most reactivated color in the presence of a substrate (e.g., ABTS) are then identified by DNA sequencing.

An enzyme reaction can be thought of as a universal protein on-switch or light switch that has a number of uses, including signal amplification, high throughput screening, and protein delivery. For signal amplification, any protein or peptide that is hydrolyzed by a protease can allow for an inhibitor to diffuse away from the active site and turn on the enzyme activity that can produce a signal. For high throughput screening, a random protein or peptide can be placed in between enzyme and the inhibitor residues to screen for novel enzymes (e.g., proteases).

Lastly, for protein delivery, an enzyme can be fused to an antibody or other protein-based drug. The fused enzyme can be used to deliver the protein to the site of disease such as a bacterial or viral infection, and/or a tumor cell. The specific hydrolysis of the fusion product releases the antibody or protein drug and delivers it at the site of the pathogen or tumor cell. In this way, the protein drug can be more precisely delivered to the area of treatment. Once delivered, the protein drug can, for example, weaken or kill the pathogen or tumor cell. In some embodiments of the invention, a bactericidal peptide can be attached to a zymogen with an activation linker that specifically reacts with, or is a target for, proteins secreted or expressed by a pathogen (e.g., bacteria). Upon finding or contacting the bacteria in the blood stream, those specific proteases from the bacteria would activate the zymogen (e.g., by reacting with a peptide substrate that is inhibiting the enzyme) and trigger the release of the bactericidal peptide, which would then destroy the bacteria. This type of targeted delivery of a bactericidal agent can reduce the chance for the bacteria to build up a drug resistance to the agent.

Further discussion of synthetic zymogen design, manufacture and use is found in U.S. Pat. No. 5,811,252, issued to Johan Hendrikus Verheijen on Sep. 22, 1998; Verheijen, J. H., et al., "Modified Proenzymes as Artificial Substrates for Proteolytic Enzymes: Colorimetric Assay of Bacterial Collagenase and Matrix Metalloproteinase Activity Using Modified Pro-Urokinase," *Biochem. J.*, 323: 603-609 (1997); Plainkum, P., et al., "Creation of a Zymogen," *Nature Struct. Biol.*, 10(2): 115-119 (2003); and Saghatelian, A., et al., "DNA Detection and Signal Amplification Via an Engineered Allosteric Enzyme," *JACS*, 125: 344-345 (2003). The entire teachings of these references are incorporated herein by reference. Additionally, examples of microorganisms, enzymes, and specific substrates for use with the present invention are found in the previously-mentioned U.S. and International applications.

Laccase (CotA)

In one embodiment, the signal enzyme is a laccase. Laccase (diphenol oxidase) is a member of the multi-copper oxidase family of enzymes. Generally, these enzymes require oxygen to oxidize phenols, polyphenols aromatic amines, and other non-phenolic substrates by one electron to create a radical species. The general oxidation reaction it catalyzes is:

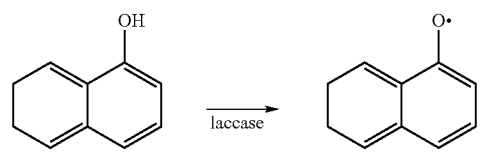

Laccase is found in fungi as well as some plants and bacteria. Laccase's natural function appears to fit two classes: formulation (sporulation or pigmentation) and degradation. Laccase is used in industrial chemistry for the bleaching and bioremediation of dyes and the degradation of lignin. It is a suitable enzyme for synthesis of a zymogen in part due to its stability and oxidation properties. The oxidation of species results in an unpaired electron which generates a color change.

Figure 6:
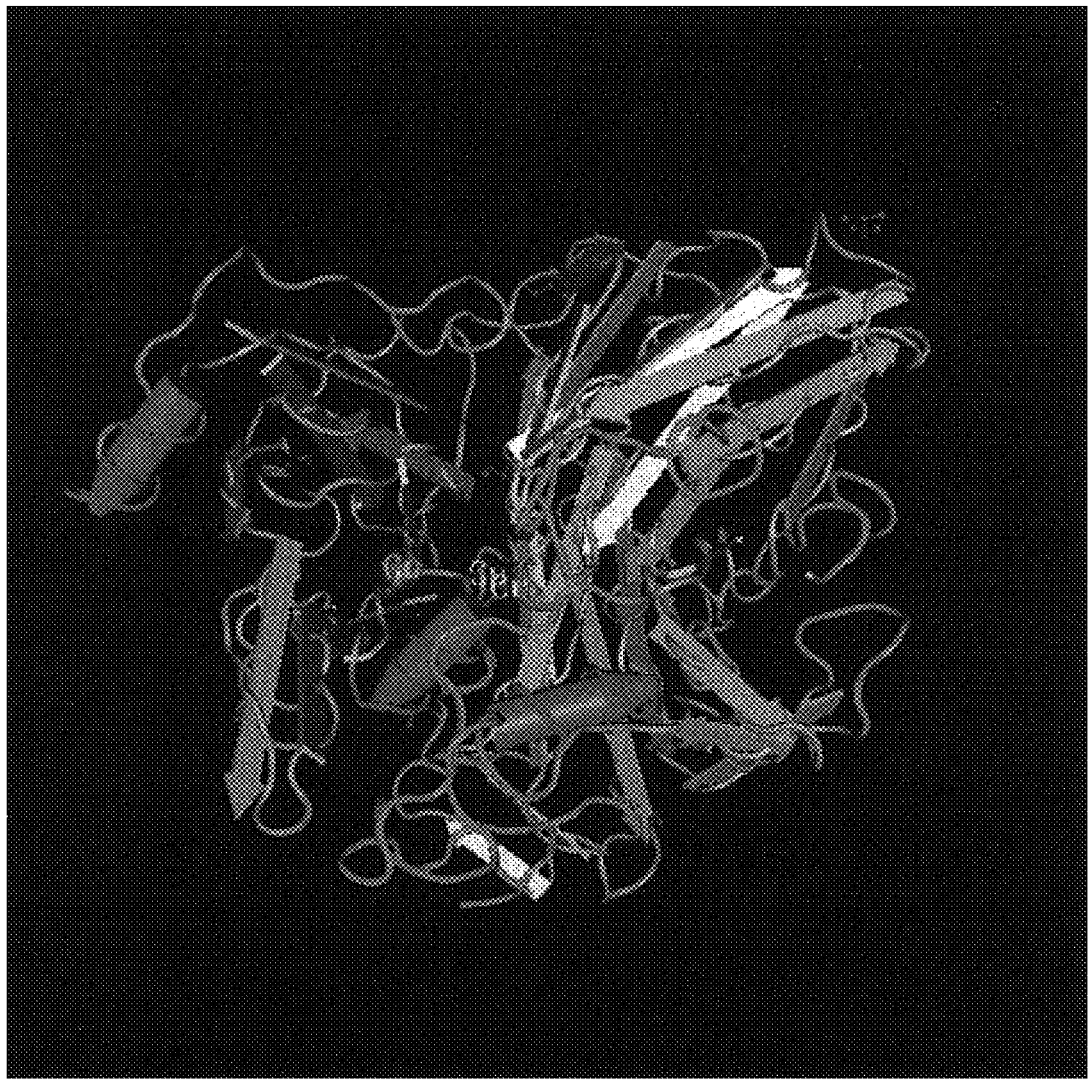
FIG. 6 illustrates *Bacillus subtilis* CotA.

FIG. 6 illustrates the *Bacillus subtilus* CotA, which is one example of a bacterial laccase. The enzyme is used in the construction of the spore coat during sporulation. (See, e.g., Enguita, F. J. et al., "Crystal Structure of a Bacterial Endospore Coat Component," *J. Biol. Chem.*, 278(21): 19416-19425 (2003), the entire contents of which is herein incorporated by reference.) The natural function of CotA appears to involve spore pigmentation for UV and $H_2O_2$ resistance. The active site appears to accept larger substrates than enzymes found in fungi and plants. CotA is highly thermostable, and can be used, for example, in a detergent base or a formalin urea base. It is not soluble, and can act as a membrane protein. One advantage of using CotA or other laccases over a simple protease approach is speed. CotA and laccase are catalytic enzymes, and, thus, much more rapid at producing a color change than a simple protease assay (generally in seconds rather than over several minutes).

The sequence of CotA is as follows:

MTLEKFVDALPIPDTLKPVQQSKEK-
TYYEVTMEECTHQLHRDLPPTRLWGYN GLFPGP-
TIEVKRNENVYVKWMNNLPSTH-
FLPIDHTIHHSDSQHEEPEVKTVVHL
HGGVTPDDSDGYPEAWFSKDFEQTGPY-
FKREVYHYPNQQRGAILWYHDHAM ALTRLNVYA-
GLVGAYIIHDPKEKRLKLPSDEYDVPL-
LITDRTINEDGSLFYPSAP
ENPSPSLPNPSIVPAFCGETILVNGKVW-
PYLEVEPRKYRFRVINASNTRTYNLSL DNGGDFI-
QIGSDGGLLPRSVKLNSFSLAPAERY-
DIIIDFTAYEGESIILANSAGCG
GDVNPETDANIMQFRVTKPLAQKDESRK-
PKYLASYPSVQHERIQNIRTLKLAGT QDEYGRPV-
LLLNNKRWHDPVTETPKVGTTEIWSI-
INPTRGTHPIHLHLVSFRVLD
RRPFDIARYQESGELSYTGPAVPP-
PPSEKGWKDTIQAHAGEVLRIAATFGPYSGR YVWH-
CHILEHEDYDMMRPMDITDPHK (*Bacillus subtilis* CotA sequence; also referred to herein as "SEQ ID NO: 1.")

CotA was used to construct a zymogen by modifying the sequence to generate a proenzyme form of the protein. Analysis of the structure of CotA indicates that an extension of suitable length appended onto the N-terminus of CotA can allow an appended inhibitor to be placed in the active site of the enzyme. The extension arm is based on the sequence of peptides shown to be cleavage targets of proteases from pathogenic bacteria. This will allow the arm to be clipped in the presence of the bacteria. In one embodiment, the peptide substrate is CPI2 or ECT2. The sequences of the peptide substrates CPI2 and ECT2 are as follows:

```
CPI2    Edans - EGAMFLEAIPMSIPK - Dabcyl

ECT2    Dabcyl - KVSRRRRRGGD - Edans
```

(the sequence EGAMFLEAIPMSIPK is also referred to herein as SEQ ID NO: 2; and the sequence KVSRRRRRGGD is also referred to herein as SEQ ID NO: 3)

Located at the end of the extension arm is the region that will interact with the active site of the enzyme. This consists of one or more amino acid residues that can inhibit the activity of CotA. This can be accomplished by binding to the active site pocket and/or to the active site copper, or by interacting with the protein structure in such a way as to cause a structural change. Analysis of the x-ray structure of CotA was used to determine the length of the amino acid chain needed to reach the shortest distance around the structure (~30 Å).

Three residues were randomized to allow for selection of the best inhibitor combination. The location of each was three amino acids from the N-terminus of the mutant form. A similar design can be generated based on the sequence of the peptide ECT2 which is specific for the *E. coli* protease OmpT.

This peptide is shorter than CPI2 and it is beneficial to add additional residues (e.g., SAS) to give it the same reach. The sequences of the additions to the N-terminus of the CotA mutant are shown below:

```
Type 1 CPI2 Mutants
MASXXXEGAMFLEAIPMSIPKTLEKFVDAL

Type 2 CPI2 Mutants
MASXXXSASEGAMFLEAIPMSIPKTLEKFVDAL

Type 3 CPI2 Mutants
MASXXXEGAMFLEAIPMSIPKSASTLEKFVDAL

Type 1 ECT2 Mutants
MASXXXSASVSRRRRRGGSASTLEKFVDAL
```

(the sequence MASXXXEGAMFLEAIPMSIPKTLEKFVDAL is also referred to herein as SEQ ID NO: 4; the sequence MASXXXSASEGAMFLEAIPMSIPKTLEKFVDAL is also referred to herein as SEQ ID NO: 5; the sequence MASXXXEGAMFLEAIPMSIPKSASTLEKFVDAL is also referred to herein as SEQ ID NO: 6; and the sequence MASXXXSASVSRRRRRGGSASTLEKFVDAL is also referred to herein as SEQ ID NO: 7).

Figure 7:
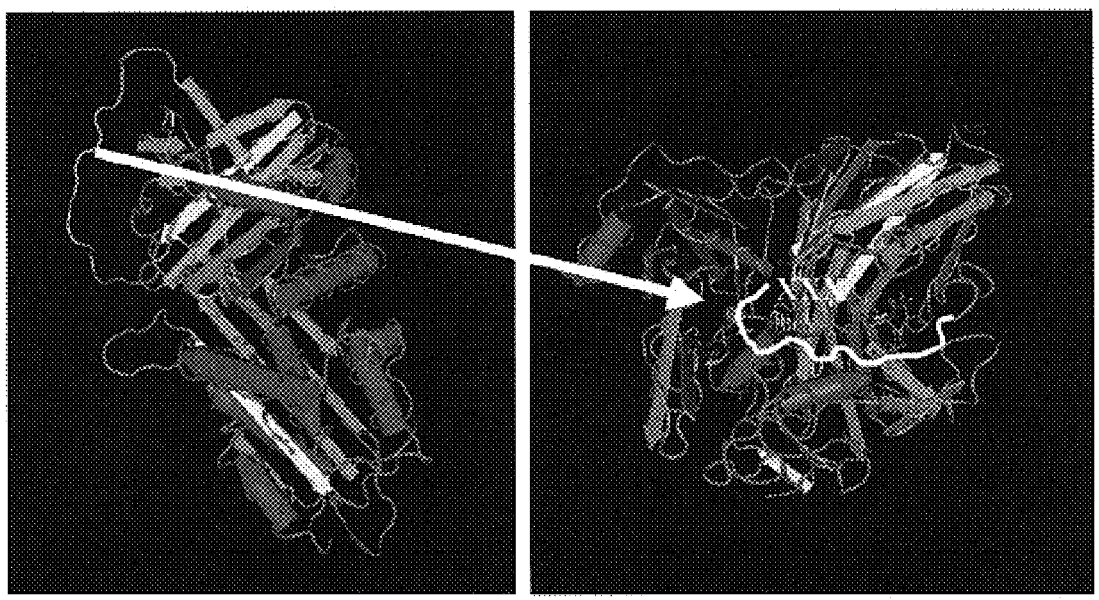
FIG. 7 shows alpha-1 proteinase reactive side loop (RSL) appended onto CotA N-terminus. The RSL region of CPI used in the CPI2 peptide sequence is shown in yellow. The same region appended onto CotA is shown in white (bold).

The alpha-1 proteinase reactive side loop (RSL) was appended onto CotA N-terminus, as shown in FIG. 7. CPI2 was based on the sequence of the reactive site loop (RSL) of alpha-1 proteinase inhibitor (also called cysteine proteinase inhibitor or CPI). Also prepared was the SSM1 CotA mutant having the sequence: MASSFWEGAMFLEAIPMSIPKTLEKFVDAL (also referred to herein as SEQ ID NO: 8).

FIG. 8 illustrates the general sequence listings resulting from CotA mutagenesis. Included in FIG. 8 are:

1. A general peptide sequence for SSM1 Mutants, the general sequence also referred to herein as SEQ ID NO: 9.
2. A general peptide sequence for SSM2 Mutants, the general sequence also referred to herein as SEQ ID NO: 10.
3. A general peptide sequence for SSM3 Mutants, the general sequence also referred to herein as SEQ ID NO: 11.
4. A general peptide sequence for SSM4 Mutants, the general sequence also referred to herein as SEQ ID NO: 12.
5. A general peptide sequence for T3 Mutants, the general sequence also referred to herein as SEQ ID NO: 13.

For Type 2 and Type 3 mutants, a three-amino acid SAS extension was inserted into the sequence to give more flexibility and a longer reach to the appended arm. One or more SAS extensions can be inserted at different points, to create a flexible linker. For example, SAS extensions can be inserted before and/or after the peptide (e.g., the CPI2 peptide), as illustrated by the following sequence, also referred to herein as "SEQ ID NO: 14":

SEQ ID NO: 14 MASXXXSASEGAMFLEAIPMSIPK-SASTLEKFVDAL

A similar procedure can also be shown for the ECT2 peptide, for example, with a set of three randomized amino acids on the end of the mutant protein.

Tethered Zymogens and Use in Detection and Diagnostics

In some embodiments, this invention features the use of a signal enzyme tethered to a solid surface (e.g., a bead) with a peptide. Some examples of suitable signal enzymes include green fluorescent protein (GFP), luciferase, laccase (CotA), and horseradish peroxidase (HRP). The peptide functions as a substrate for a microbial protein (e.g., a bacterial enzyme, such as a bacterial protease). When the peptide interacts with the microbial protein of interest, the peptide is cleaved or hydrolyzed by the microbial protein. This interaction releases the signal enzyme, and the signal enzyme is then free to interact with a reporter or detectably labeled substrate and produce a detectable signal indicating the presence of the microbe of interest. Examples of suitable reporter substrates includes ABTS and naphthol.

In some embodiments, the signal enzyme substrate can be bound or tethered to a surface, such as a lateral flow membrane or bead (e.g., one made out of nitrocellulose). One portion of the membrane can comprise the tethered signal enzyme, while another portion of the membrane can comprise a detectably labeled substrate. A liquid test sample is introduced onto the portion of the membrane comprising the tethered signal enzyme. If the liquid test sample includes the microbial protein of interest, the microbial protein cleaves the peptide and the activated enzyme is freed. The activated enzyme then migrates towards the portion of the membrane where the detectably labeled substrate is located. Once the activated signal enzyme reaches the portion of the membrane that includes the detectably labeled substrace, the signal enzyme interacts with the detectably labeled substrate and produces a visible signal.

Multiple pathogens or enzymes can be detected in series on the same lateral flow membrane by forming a channel in the membrane with wax or other material(s) that make the membrane material impervious to proteins and substrates but allows liquid or buffer to flow. As an example, parafilm wax can be dissolved in hexane and used to partition the sample into multiple chambers (e.g., channels or lanes). This would be a cost effective way to have multiple lateral flow tests to detect the presence of pathogenic bacteria within one single lateral flow membrane, thereby reducing the cost of each test.

Figure 15:
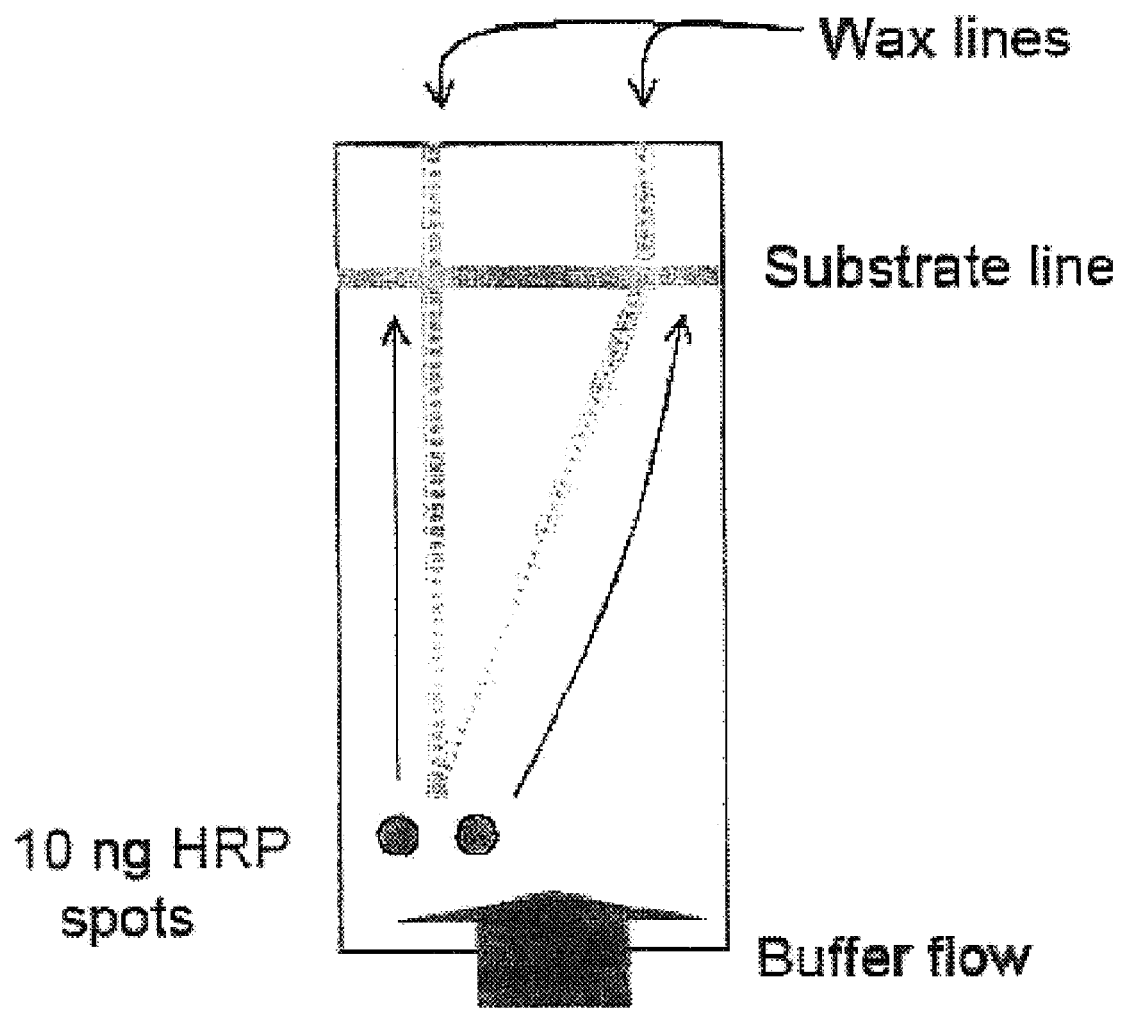
FIG. 15 illustrates a diagram of one embodiment of a multi-channel lateral flow membrane.

FIG. 15 illustrates a diagram of one embodiment of a multi-channel lateral flow membrane. Wax (e.g., parafilm wax) is dissolved in hexane and laid down onto a POREX® lateral flow membrane (available from Porex Technologies Corp., Fairburn Ga.) using a pipette tip. A sample to be tested is placed on or near the 10 ng HRP spots located at the bottom end of the membrane. The sample interacts with the tethered zymogen, and begins to flow towards the substrate line via the wax lines or lanes. If the microbial protein of interest is present in the testing sample, the signal enzyme will be released, and the now-active enzyme will migrate to the substrate line along with the testing sample. Once the active signal enzyme reaches the substrate line, the enzyme will interact with the detectably labeled substrate and produce a visible signal (e.g., a visible line).

In addition to lateral flow and liquid phase diagnostics, the tethered zymogens can also be used in a high throughput screen (HTS) for novel diagnostic targets. For example, a screen can use green fluorescent protein (e.g., GFP) synthetically fused to a random 10 amino acid region attached to a C-terminal epitope tag (e.g., poly-histidine). The epitope tag allows for the reporter system to be tethered to a surface until a specific enzyme hydrolysis event from microbial protein (e.g., a bacterial protease) triggers the release of the reporting enzyme.

Figure 16:
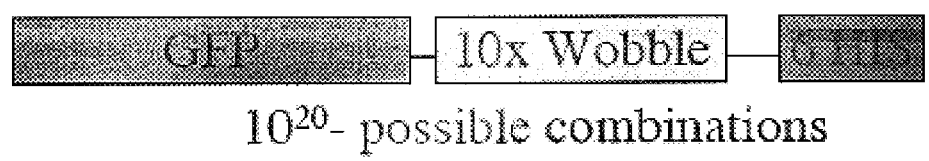
FIG. 16 illustrates a photograph of a DNA gel (on the left) alongside a photograph of a protein gel (on the right).
Figure 16:
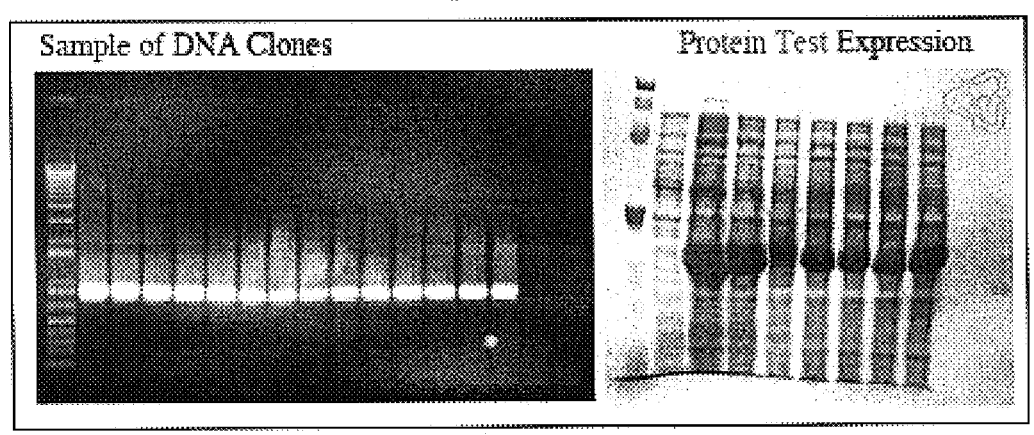

Using PCR, a GFP library of random peptides has been amplified and cloned to make a high throughput screen to detect the presence of specific proteolytic events. The screen can be used to identify novel substrates for bacterial pathogens that could be incorporated into a rapid point of care diagnostic. FIG. 16 illustrates a photograph of a DNA gel (on the left) along side a photograph of a protein gel (on the right). The DNA gel of the left demonstrates a sample of ten clones from the library that all have GFP, and the protein gel on the right indicates that all the clones are expressing GFP. Since the clones can be bound to a resin or beads that bind the epitope tag, these protein products are suitable for high throughput screens using microtiter plates in the 96, 386, or greater well formats that allows for the rapid processing of cells.

Figure 5:
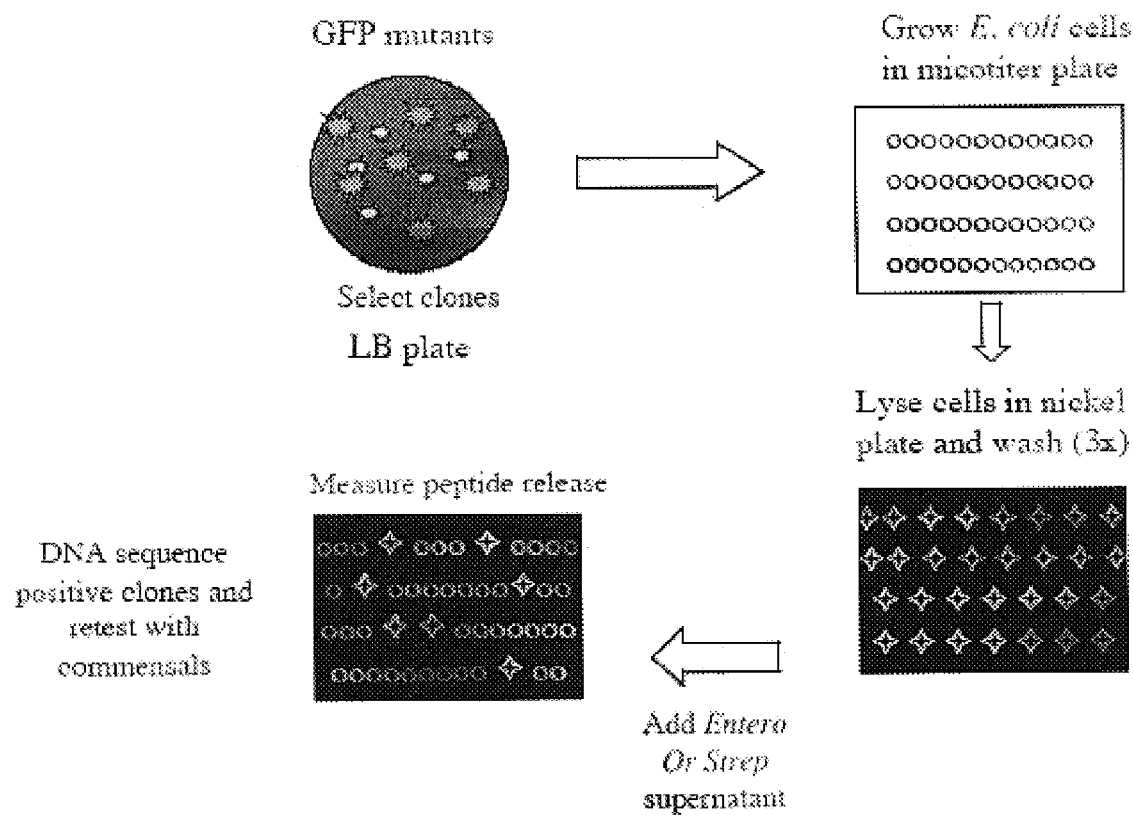
FIG. 5 illustrates a process by which individual clones can be identified using methods of this invention.

The process by which individual clones can be identified using this method is illustrated in FIG. 5. Briefly, the cells are grown and then lysed in a microtiter plate containing 50 μg of lysozyme and 100 U of DNAse I. The cell debris is removed by centrifuging and the GFP supernatants are bound to plates containing NTA resin to specifically bind the protein. Upon washing the protein, each well is incubated with a bacterial culture and then centrifuged through a spin filter to separate the bound GFP from the free GFP. Samples that specifically release the GFP are retested with other bacteria to see if they are specific and then DNA sequenced to identify the clone. One of the clones is identified. The peptide can be synthesized and then covalently attached or engineered onto CotA or HRP for the development of a novel rapid diagnostic assay.

EXAMPLE 1

Cloning and Expression of Wildtype and Mutant CotA Variants

Oligonucleotide primers (illustrated in Table 1) were designed to incorporate an NheI restriction site at the 5' end and a XhoI site at the 3' end of the gene during the amplification of CotA variants from *Bacillus subtilis* (restriction sites are underlined in Table 1). The PCR-amplified fragment was cloned into the NheI/XhoI site of expression vector pET24a (Novagen, San Diego, Calif.) to generate recombinant SSM plasmids (Table 2).

Figure 9:
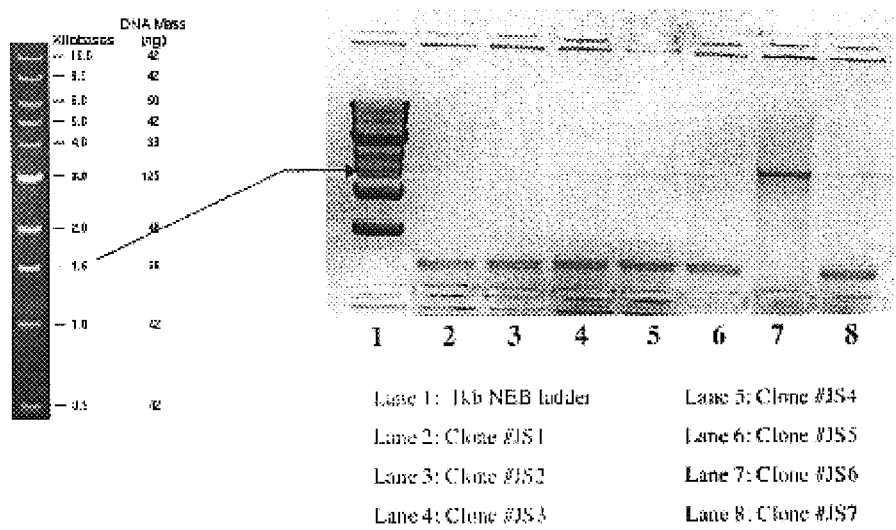
FIG. 9 illustrates a photograph confirming insertion of 1.7 kb wild-type CotA.

Colony PCR using a commercially available T7 primer set confirmed the presence of the insert in the recombinant SSM constructs. FIG. 9 illustrates a photograph of the resulting PCR gel, confirming the insertion of 1.7 kb wild-type CotA by PCR. The vector is pET24A, the insert is wild-type CotA, and the primer set used was a commercially available T7 primer set. Lane 7 shows Clone JS6, indicating an insert size of ~1.542 kb.

TABLE 1

Oligonucleotide primers

| Primer | Sequence |
|---|---|
| CotAFor | CATATGGCTAGCACACTTGAAAAATTTGTGGATGCTCTC |
| MutantFORcotA | CTAGCTAGCNNNNNNNNNNGAAGGA GCA ATGTTC CTA GAA GCA ATA CCA ATG TCA ATA CCA AAA ACA CTT GAA AAA TTTGTGGAT GCT CTC |
| CTAFE1 | CTAGCTAGCNNNNNNNNNNTCA GCA TCA GAAGGA GCA ATGTTC CTA GAA GCA ATA CCA ATG TCA ATA CCA AAA ACA CTT GAA AAA TTTGT GGAT GCT CTC |
| CTAFE2 | CTAGCTAGCNNNNNNNNNNGAAGGAGCAATGTTCCTAG AAGCAATACCAATGTCA ATA CCA AAATCAGCA TCA ACA CTT GAA AAATTTGTGGATGCTCTC |
| NewCMF | CTAGCTAGCGAAGGA GCA ATGTTC CTA GAA GCA ATA CCA ATG TCA ATA CCA AAA ACA CTT GAA AAA TTTGTGGAT GCT CTC |
| CotA Rev | CCGCTCGAGTTATTTATGGGGATCAGTTATATCC |

(CotAFor is also referred to herein as "SEQ ID NO: 15"; MutantFORcotA is also referred to herein as "SEQ ID NO:

16"; CTAFE1 is also referred to herein as "SEQ ID NO: 17"; CTAFE2 is also referred to herein as "SEQ ID NO: 18"; NewCMF is also referred to herein as "SEQ ID NO: 19"; and CotA Rev is also referred to herein as "SEQ ID NO: 20")

TABLE 2

Recombinant plasmids

| Recombinant plasmids | Description |
|---|---|
| JS6 | COTA |
| SSM1 | COTA-CPI2-XXX |
| SSM2 | COTA-CPI2-SAS-XXX |
| SSM3 | COTA-SAS-CPI2-XXX |
| SSM4 | COTA-CPI2 |

EXAMPLE 2

Expression of Wildtype and CotA Variants

Figure 10:
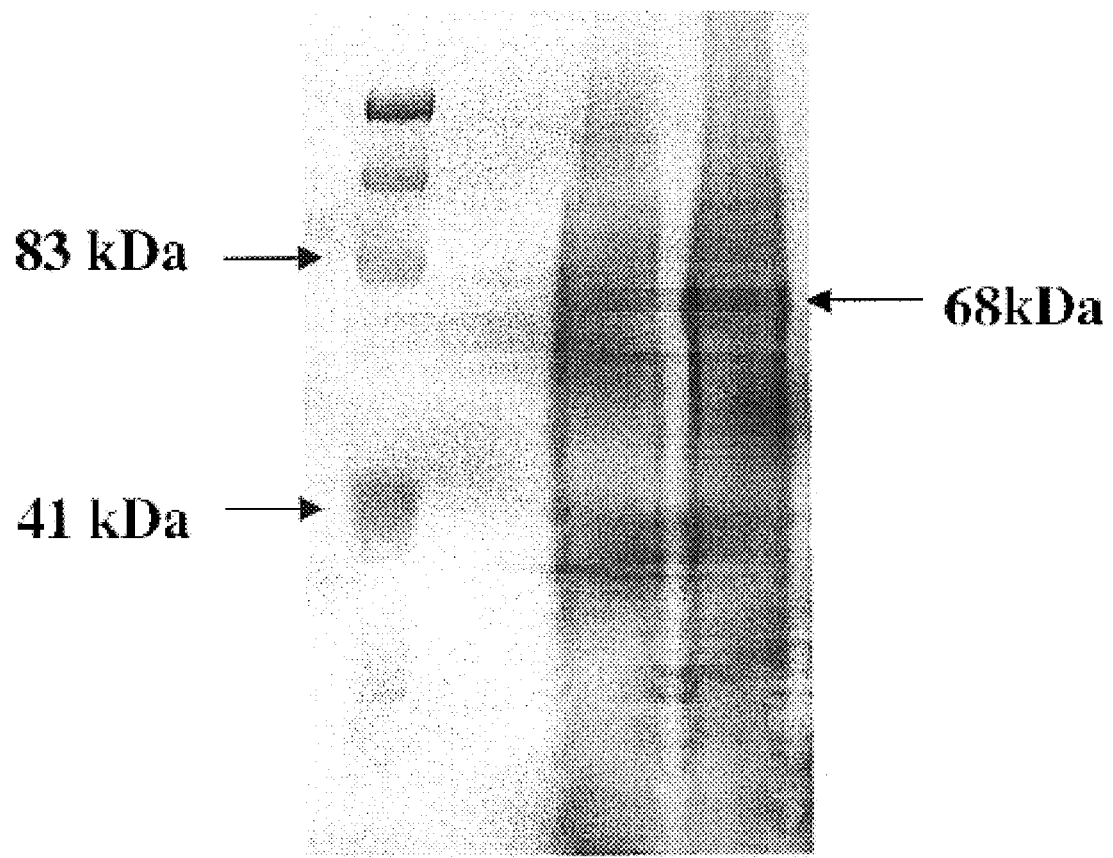
FIG. 10 illustrates a photograph of the gel showing overexpression of CotA in clone JS6.

To express the CotA variants, the SSM constructs were transformed into E. coli expression strain BL21DE3. At an optical density at 550 nm of 0.4, the cells were induced by the addition of 1 mM isopropyl-β-D-thiogalactopyranoside (IPTG; Sigma, St. Louis, Mo.) and growth continued at 37° C. for 3 hours. Following induction, 1 ml of the cells was centrifuged and resuspended in 50 μl of PSB (protein sample buffer), boiled for 10 min and electrophoresed at 200V for 1 hour. The expression was confirmed by running a protein sample on a 12% SDS PAGE gel. Overexpression of CotA in clone JS6 was also demonstrated. FIG. 10 illustrates a photograph of the gel showing the overexpression of CotA in clone JS6.

Figure 11:
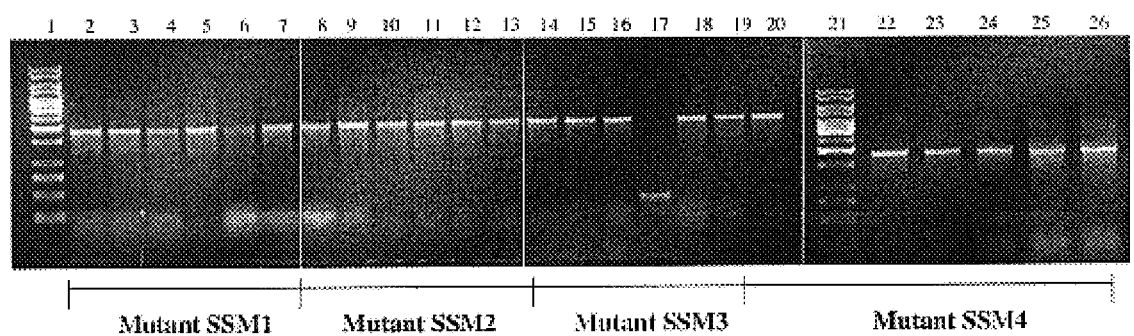
FIG. 11 illustrates a photograph of a PCR screening gel of CotA mutants using T7 primer set.
Figure 12:
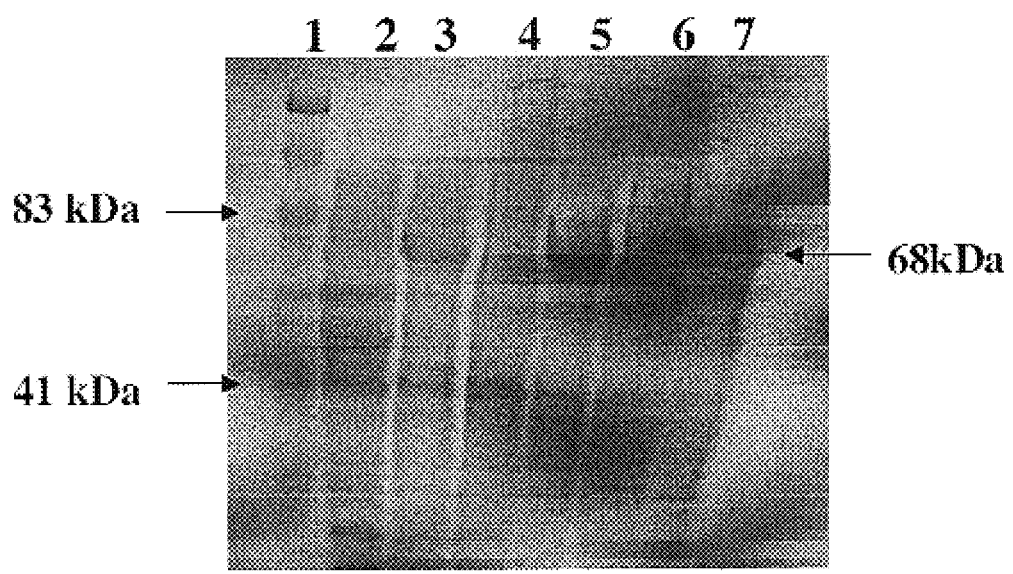
FIG. 12 illustrates a photograph of a gel showing the overexpression of mutant CotA (SSM1) in clone JS6.

FIG. 11 illustrates a photograph of a gel demonstrating PCR screening of CotA mutants using T7 primer set. FIG. 12 illustrates a photograph of a gel showing the overexpression of mutant CotA using SSM1 clones.

EXAMPLE 3

ABTS Assay of Wildtype and Mutant Variants of CotA

Figure 13:
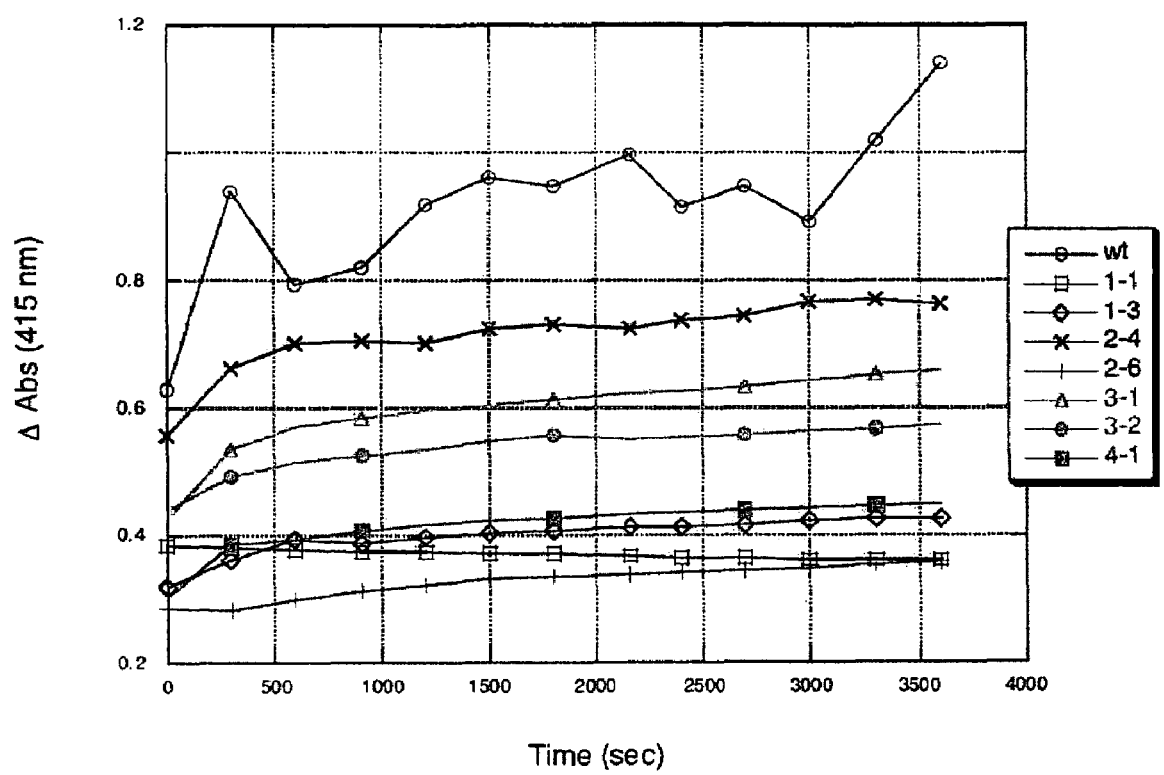
FIG. 13 illustrates a graph showing that CotA variants were partially inhibited by extension and modification of CotA.

The activity of CotA wild type and the mutant variants was determined using an 2,2'-azinobis(3-ethylbenzthiazoline-6-sulfonate) (ABTS) assay. Briefly, 45 μl of the wild type and mutant CotA lysates were incubated with 10 μl of ABTS substrate (2.0 mM) and 45 μl of 1× phosphate buffered saline (PBS). The reaction was followed on a 96 well microtiter plate reader using an wavelength of 415 nm at 37° C. The reaction was monitored for a period of 1 hour (hr) and plotted using the KaleidaGraph software. As expected, the wild type had the highest reactivity to the ABTS substrate when compared to the CotA mutant variants. FIG. 13 illustrates a graph showing that the CotA variants (SSM4-1, SSM1-1, SSM1-3, SSM2-4, and SSM2-6) were partially inhibited by the extensions and modifications of CotA. In FIG. 13, "wt" refers to wild-type, "1-1" refers to SSM1-1, "1-3" refers to SSM1-3, "2-4" refers to SSM2-4, "2-6" refers to SSM2-6, "3-1" refers to SSM3-1, "3-2" refers to SSM3-2, and "4-1" refers to SSM4-1.

Figure 14:
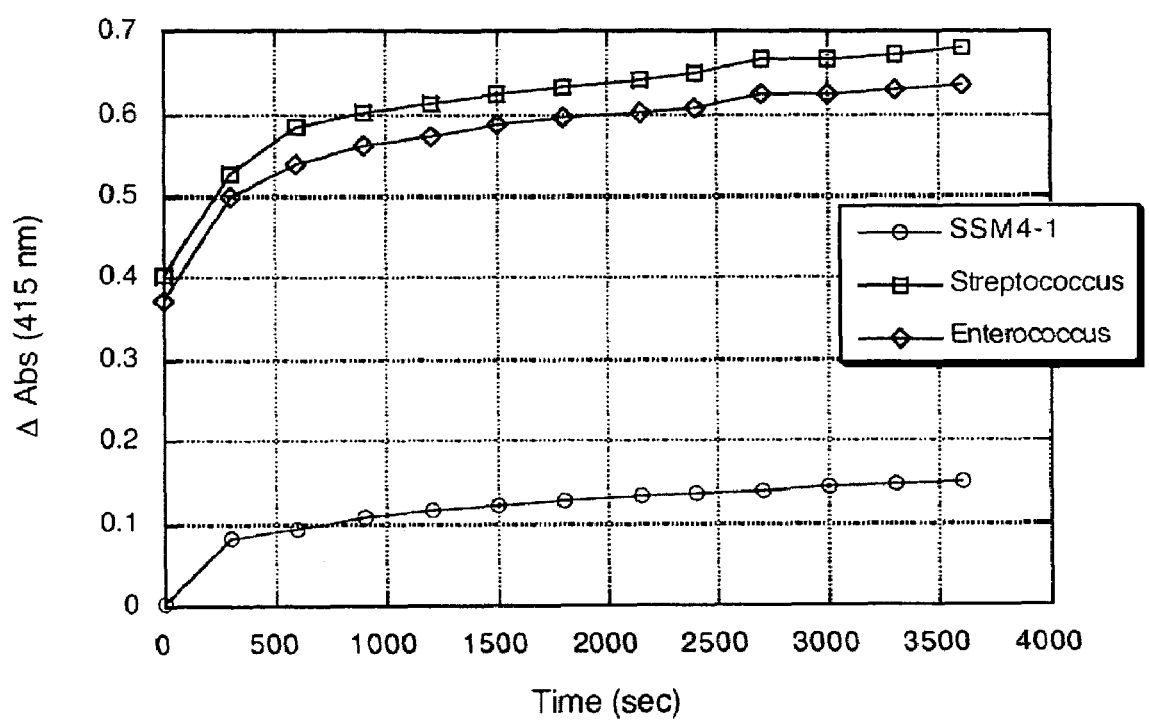
FIG. 14 illustrates a graph of the reactivation of the CotA mutant SSM4-1.

The activity of the CotA mutant, SSM4-1 was partially inhibited as determined by the ABTS assay, as shown in graph illustrated in FIG. 14. However, the presence of bacterial supernatants from Streptococcus pyogenes and Enterococcus faecalis in similar assays facilitated the reactivations of SSM4-1 mutant approximately by three-fold. The specific proteases from the bacterial supernatants cleave the CPI2 domain of SSM4-1 mutant, resulting in de-repression of inhibitory phenotype. The ABTS assays were performed as previously described. Briefly, the control mix consists of 10 μg of ABTS, 0.2 mM $CuSO_4$, 10% glycerol, 0.1% HECAMEG detergent in 1× phosphate buffered saline. The reactivation mix consists of 10 μl of ABTS (2.0 mM), 20 μl of cultured bacterial supernatant, 0.2 mM $CuSO_4$, 10% glycerol, 0.1% HECAMEG detergent in 1× phosphate buffered saline. The bacterial cultures (S. pyogenes and E. faecalis) used in this assay were grown overnight in tryptic soy broth (TSB).

EXAMPLE 4

Tethering Zymogens With Peptides

Signal enzymes were tethered or conjugated to solid surfaces with a variety of peptides. Examples of peptides which were successfully used to tether the signal enzymes include:

1. SAP2, having the sequence: ETKVEENEAIQK (also referred to herein as SEQ ID NO: 21)

2. C10, having the sequence: VTLENTALARC (also referred to herein as SEQ ID NO: 22)

3. PAE8, having the sequence: QADALHDQASALKC (also referred to herein as SEQ ID NO: 23)

4. CPI2, having the sequence indicated in SEQ ID NO: 2

5. T2X, having the sequence: KVSRRRRRGGDKVSR-RRRRGGD (also referred to herein as SEQ ID NO: 24)

SAP2 and C10 are specific for Staphylococcus, PAE8 is specific for Pseudomonas, T2 is specific to E. coli, and CPI2 is a peptide that interacts with a broad spectrum of pathogens. In addition, various random peptides with a 10 amino acid variable sequence were also successfully used to tether signal enzymes to solid surfaces.

Conjugation of HRP to peptides was done through the bi-functional crosslinking reagent sulfo-SMCC. The reaction is a two step process, including 1) formation of HRP-maleimide, followed by 2) reaction with a peptide. The peptide-HRP conjugates gave visible blue color after being hydrolyzed from the tethered surface. The general protocol for the conjugation was:

Peptide Attachment to Biodyne C 1 mg of peptide was dissolved in conjugation buffer (MES pH 4.5). 125 μl of 10 mg/ml EDC (5:1 ratio) was added and allowed to react with membranes during 2 hours of rotation at room temperature. Room temperature washes were performed for 20 minues with 40 mL of PBS+1% glycerol and PBS.

HRP Maleimide Conjugation 2.5 mg of Roche HRP was dissolved in 500 μl of 1M Na phosphate (pH of 7.4). Sulfo-SMCC was dissolved in 50 μl DMSO, and combined with the HRP for 20 minutes at room temperature. Separation was accomplished with Gel filtration in maleimide conjugation buffer.

HRP-Peptide-Membrane Conjugation

The fractions that were free of sulfo-SMCC (~1 ml) were combine with the peptide-Biodyne disks and reacted at ~4° C. overnight with rotation. Several washes were conducted, including two 20-minute washes with 100 mL of 0.1% triton in PBS, followed by two 20-minute washes with 0.1% PEG 5000 solution, and a 1 hr wash in 250 mL of a 10% sucrose solution, followed by speed vacuuming overnight.

EXAMPLE 5

Tethered Zymogens Assay

The tethered zymogens can be used in a liquid phase approach, or a lateral flow membrane approach. In the lateral flow membrane approach, the detectably labeled substrate or reporter enzyme is captured or adhered on with liquid nitrocellulose that is deposited on the surface of a lateral flow membrane to form a visible line following the diffusion of the reporter enzyme.

A line of 1% highly purified nitrocellulose in amyl acetate (CAT#12620-50, from Electron Microscopy Science) mixed at a volumetric ratio of 1:1 with naphthol was deposited on a membrane. The membrane was about 3 centimeters long. The final concentration in the solution before deposition was 10 mg/ml nitrocellulose and 20 mg/ml naphthol. Upon release from the tethered peptide surface, a CotA and HRP enzyme migrated down the surface of the lateral flow chamber. Upon interacting with the naphthol bound to the deposited nitrocellulose, a dark blue line formed in just a few seconds, indicating the presence of the bacterial pathogen.

---

What is claimed is:

1. A testing device, comprising:
   a) a membrane;
   b) at least one peptide attached to the membrane, the peptide comprising a substrate for an enzyme produced by a microorganism;
   c) a signal enzyme attached to the peptide; and
   d) at least one detectably labeled substrate attached to the membrane at a second location such that the signal enzyme cannot react with the labeled substrate prior to the action of the enzyme produced by the microorganism, the detectably labeled substrate being a target of the signal enzyme.

* * * * *

SEQUENCE LISTING

<160> NUMBER OF SEQ ID NOS: 24

<210> SEQ ID NO 1
<211> LENGTH: 513
<212> TYPE: PRT
<213> ORGANISM: Bacillus subtilis CotA

<400> SEQUENCE: 1

```
Met Thr Leu Glu Lys Phe Val Asp Ala Leu Pro Ile Pro Asp Thr Leu
1               5                  10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
```

```
                275                 280                 285
Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln His Glu Arg Ile Gln Asn
        355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Thr
385                 390                 395                 400

Pro Lys Val Gly Thr Thr Glu Ile Trp Ser Ile Ile Asn Pro Thr Arg
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Ser Gly Glu Leu Ser
        435                 440                 445

Tyr Thr Gly Pro Ala Val Pro Pro Pro Ser Glu Lys Gly Trp Lys
    450                 455                 460

Asp Thr Ile Gln Ala His Ala Gly Glu Val Leu Arg Ile Ala Ala Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510
Lys

<210> SEQ ID NO 2
<211> LENGTH: 15
<212> TYPE: PRT
<213> ORGANISM: Artificial Sequence
<220> FEATURE:
<223> OTHER INFORMATION: Peptide Substrate CPI2

<400> SEQUENCE: 2

Glu Gly Ala Met Phe Leu Glu Ala Ile Pro Met Ser Ile Pro Lys
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Peptide Substrate ECT2

<400> SEQUENCE: 3

Lys Val Ser Arg Arg Arg Arg Arg Gly Gly Asp
1               5                   10

<210> SEQ ID NO 4
<211> LENGTH: 30
<212> TYPE: PRT
<213> ORGANISM: Artificial Sequence
<220> FEATURE:
<223> OTHER INFORMATION: Type 1 CPI2 Mutants
```

```
<220> FEATURE:
<221> NAME/KEY: VARIANT
<222> LOCATION: (1)...(30)
<223> OTHER INFORMATION: Xaa = Any Amino Acid

<400> SEQUENCE: 4

Met Ala Ser Xaa Xaa Xaa Glu Gly Ala Met Phe Leu Glu Ala Ile Pro
 1               5                  10                  15

Met Ser Ile Pro Lys Thr Leu Glu Lys Phe Val Asp Ala Leu
            20                  25                  30

<210> SEQ ID NO 5
<211> LENGTH: 33
<212> TYPE: PRT
<213> ORGANISM: Artificial Sequence
<220> FEATURE:
<223> OTHER INFORMATION: Type 2 CPI2 Mutants
<220> FEATURE:
<221> NAME/KEY: VARIANT
<222> LOCATION: (1)...(33)
<223> OTHER INFORMATION: Xaa = Any Amino Acid

<400> SEQUENCE: 5

Met Ala Ser Xaa Xaa Xaa Ser Ala Ser Glu Gly Ala Met Phe Leu Glu
 1               5                  10                  15

Ala Ile Pro Met Ser Ile Pro Lys Thr Leu Glu Lys Phe Val Asp Ala
            20                  25                  30

Leu

<210> SEQ ID NO 6
<211> LENGTH: 33
<212> TYPE: PRT
<213> ORGANISM: Artificial Sequence
<220> FEATURE:
<223> OTHER INFORMATION: Type 3 CPI2 Mutants
<220> FEATURE:
<221> NAME/KEY: VARIANT
<222> LOCATION: (1)...(33)
<223> OTHER INFORMATION: Xaa = Any Amino Acid

<400> SEQUENCE: 6

Met Ala Ser Xaa Xaa Xaa Glu Gly Ala Met Phe Leu Glu Ala Ile Pro
 1               5                  10                  15

Met Ser Ile Pro Lys Ser Ala Ser Thr Leu Glu Lys Phe Val Asp Ala
            20                  25                  30

Leu

<210> SEQ ID NO 7
<211> LENGTH: 30
<212> TYPE: PRT
<213> ORGANISM: Artificial Sequence
<220> FEATURE:
<223> OTHER INFORMATION: Type 1 ECT2 Mutants
<220> FEATURE:
<221> NAME/KEY: VARIANT
<222> LOCATION: (1)...(30)
<223> OTHER INFORMATION: Xaa = Any Amino Acid

<400> SEQUENCE: 7

Met Ala Ser Xaa Xaa Xaa Ser Ala Ser Val Ser Arg Arg Arg Arg
 1               5                  10                  15

Gly Gly Ser Ala Ser Thr Leu Glu Lys Phe Val Asp Ala Leu
            20                  25                  30

<210> SEQ ID NO 8
```

```
<211> LENGTH: 30
<212> TYPE: PRT
<213> ORGANISM: Artificial Sequence
<220> FEATURE:
<223> OTHER INFORMATION: SSM1 CotA Mutant

<400> SEQUENCE: 8

Met Ala Ser Ser Phe Trp Glu Gly Ala Met Phe Leu Glu Ala Ile Pro
1               5                   10                  15

Met Ser Ile Pro Lys Thr Leu Glu Lys Phe Val Asp Ala Leu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: SSM1 CotA Mutants
<220> FEATURE:
<221> NAME/KEY: VARIANT
<222> LOCATION: (1)...(30)
<223> OTHER INFORMATION: Xaa = Any Amino Acid

<400> SEQUENCE: 9

Met Ala Ser Xaa Xaa Xaa Glu Gly Ala Met Phe Leu Glu Ala Ile Pro
1               5                   10                  15

Met Ser Ile Pro Lys Thr Leu Glu Lys Phe Val Asp Ala Leu
            20                  25                  30

<210> SEQ ID NO 10
<211> LENGTH: 33
<212> TYPE: PRT
<213> ORGANISM: Artificial Sequence
<220> FEATURE:
<223> OTHER INFORMATION: SSM2 CotA Mutants
<220> FEATURE:
<221> NAME/KEY: VARIANT
<222> LOCATION: (1)...(33)
<223> OTHER INFORMATION: Xaa = Any Amino Acid

<400> SEQUENCE: 10

Met Ala Ser Xaa Xaa Xaa Ser Ala Ser Glu Gly Ala Met Phe Leu Glu
1               5                   10                  15

Ala Ile Pro Met Ser Ile Pro Lys Thr Leu Glu Lys Phe Val Asp Ala
            20                  25                  30

Leu

<210> SEQ ID NO 11
<211> LENGTH: 33
<212> TYPE: PRT
<213> ORGANISM: Artificial Sequence
<220> FEATURE:
<223> OTHER INFORMATION: SSM3 CotA Mutants
<220> FEATURE:
<221> NAME/KEY: VARIANT
<222> LOCATION: (1)...(33)
<223> OTHER INFORMATION: Xaa = Any Amino Acid

<400> SEQUENCE: 11

Met Ala Ser Xaa Xaa Xaa Glu Gly Ala Met Phe Leu Glu Ala Ile Pro
1               5                   10                  15

Met Ser Ile Pro Lys Ser Ala Ser Thr Leu Glu Lys Phe Val Asp Ala
            20                  25                  30

Leu
```

<210> SEQ ID NO 12
<211> LENGTH: 27
<212> TYPE: PRT
<213> ORGANISM: Artificial Sequence
<220> FEATURE:
<223> OTHER INFORMATION: SSM4 CotA Mutants

<400> SEQUENCE: 12

Met Ala Ser Glu Gly Ala Met Phe Leu Glu Ala Ile Pro Met Ser Ile
1               5                   10                  15

Pro Lys Thr Leu Glu Lys Phe Val Asp Ala Leu
            20                  25

<210> SEQ ID NO 13
<211> LENGTH: 30
<212> TYPE: PRT
<213> ORGANISM: Artificial Sequence
<220> FEATURE:
<223> OTHER INFORMATION: T3 CotA Mutants
<220> FEATURE:
<221> NAME/KEY: VARIANT
<222> LOCATION: (1)...(30)
<223> OTHER INFORMATION: Xaa = Any Amino Acid

<400> SEQUENCE: 13

Met Ala Ser Xaa Xaa Xaa Ser Ala Ser Val Ser Arg Arg Arg Arg
1               5                   10                  15

Gly Gly Ser Ala Ser Thr Leu Glu Lys Phe Val Asp Ala Leu
            20                  25                  30

<210> SEQ ID NO 14
<211> LENGTH: 36
<212> TYPE: PRT
<213> ORGANISM: Artificial Sequence
<220> FEATURE:
<223> OTHER INFORMATION: CPI2 Mutants
<220> FEATURE:
<221> NAME/KEY: VARIANT
<222> LOCATION: (1)...(36)
<223> OTHER INFORMATION: Xaa = Any Amino Acid

<400> SEQUENCE: 14

Met Ala Ser Xaa Xaa Xaa Ser Ala Ser Glu Gly Ala Met Phe Leu Glu
1               5                   10                  15

Ala Ile Pro Met Ser Ile Pro Lys Ser Ala Ser Thr Leu Glu Lys Phe
            20                  25                  30

Val Asp Ala Leu
        35

<210> SEQ ID NO 15
<211> LENGTH: 39
<212> TYPE: DNA
<213> ORGANISM: Artificial Sequence
<220> FEATURE:
<223> OTHER INFORMATION: Oligonucleotide primer CotAFor

<400> SEQUENCE: 15
catatggcta gcacacttga aaaatttgtg gatgctctc                      39

<210> SEQ ID NO 16
<211> LENGTH: 90
<212> TYPE: DNA
<213> ORGANISM: Artificial Sequence
<220> FEATURE:
<223> OTHER INFORMATION: Oligonucleotide primer MutantForCotA
<220> FEATURE:
<221> NAME/KEY: misc_feature -continued

```
<222> LOCATION: (1)...(90)
<223> OTHER INFORMATION: n = A,T,C or G

<400> SEQUENCE: 16
ctagctagcn nnnnnnnnga aggagcaatg ttcctagaag caataccaat gtcaatacca      60
aaaacacttg aaaaatttgt ggatgctctc                                      90

<210> SEQ ID NO 17
<211> LENGTH: 99
<212> TYPE: DNA
<213> ORGANISM: Artificial Sequence
<220> FEATURE:
<223> OTHER INFORMATION: Oligonucleotide primer CTAFE1
<220> FEATURE:
<221> NAME/KEY: misc_feature
<222> LOCATION: (1)...(99)
<223> OTHER INFORMATION: n = A,T,C or G

<400> SEQUENCE: 17
ctagctagcn nnnnnnntc agcatcagaa ggagcaatgt tcctagaagc aataccaatg      60
tcaataccaa aaacacttga aaatttgtg gatgctctc                             99

<210> SEQ ID NO 18
<211> LENGTH: 99
<212> TYPE: DNA
<213> ORGANISM: Artificial Sequence
<220> FEATURE:
<223> OTHER INFORMATION: Oligonucleotide primer CTAFE2
<220> FEATURE:
<221> NAME/KEY: misc_feature
<222> LOCATION: (1)...(99)
<223> OTHER INFORMATION: n = A,T,C or G

<400> SEQUENCE: 18 tagctagcn nnnnnnnga aggagcaatg ttcctagaag caataccaat gtcaatacca       60
aaatcagcat caacacttga aaatttgtg gatgctctc                             99

<210> SEQ ID NO 19
<211> LENGTH: 81
<212> TYPE: DNA
<213> ORGANISM: Artificial Sequence
<220> FEATURE:
<223> OTHER INFORMATION: Oligonucleotide primer NewCMF

<400> SEQUENCE: 19
ctagctagcg aaggagcaat gttcctagaa gcaataccaa tgtcaatacc aaaaacactt     60
gaaaaatttg tggatgctct c                                               81

<210> SEQ ID NO 20
<211> LENGTH: 34
<212> TYPE: DNA
<213> ORGANISM: Artificial Sequence
<220> FEATURE:
<223> OTHER INFORMATION: Oligonucleotide primer CotA Rev

<400> SEQUENCE: 20
ccgctcgagt tatttatggg gatcagttat atcc                                 34

<210> SEQ ID NO 21
<211> LENGTH: 12
<212> TYPE: PRT
<213> ORGANISM: Artificial Sequence
<220> FEATURE:
<223> OTHER INFORMATION: SAP2
```

```
<400> SEQUENCE: 21

Glu Thr Lys Val Glu Glu Asn Glu Ala Ile Gln Lys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: C10

<400> SEQUENCE: 22

Val Thr Leu Glu Asn Thr Ala Leu Ala Arg Cys
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: PAE8

<400> SEQUENCE: 23

Gln Ala Asp Ala Leu His Asp Gln Ala Ser Ala Leu Lys Cys
 1               5                  10

<210> SEQ ID NO 24
<211> LENGTH: 22
<212> TYPE: PRT
<213> ORGANISM: Artificial Sequence
<220> FEATURE:
<223> OTHER INFORMATION: T2X

<400> SEQUENCE: 24

Lys Val Ser Arg Arg Arg Arg Gly Gly Asp Lys Val Ser Arg Arg
 1               5                  10                  15

Arg Arg Arg Gly Gly Asp
                20
```